United States Patent [19]

Lo

[11] Patent Number: 4,990,683
[45] Date of Patent: Feb. 5, 1991

[54] PROCESS FOR PREPARING 3-PYRROLIDINOLS

[75] Inventor: Young S. Lo, Richmond, Va.

[73] Assignee: A. H. Robins Company, Incorporated, Richmond, Va.

[21] Appl. No.: 141,740

[22] Filed: Jan. 11, 1988

Related U.S. Application Data

[62] Division of Ser. No. 923,544, Oct. 27, 1986, abandoned.

[51] Int. Cl.$^5$ .................. C07C 255/12; C07C 255/36
[52] U.S. Cl. .................................. 558/390; 558/393; 558/451
[58] Field of Search .................................. 558/390, 451

[56] References Cited

U.S. PATENT DOCUMENTS

| | | | |
|---|---|---|---|
| 2,830,997 | 4/1958 | Lunsford | 548/541 |
| 2,838,521 | 6/1958 | Lunsford | 548/556 |
| 2,882,276 | 4/1959 | Lunsford | 548/556 |
| 2,956,062 | 10/1960 | Lunsford | 548/556 |
| 3,150,131 | 9/1964 | Fulmer et al. | 558/390 X |
| 3,301,869 | 1/1967 | Lunsford | 548/556 |
| 3,444,137 | 5/1969 | Higginbottom et al. | 558/390 X |
| 4,592,866 | 6/1986 | Cale, Jr. | 540/490 X |

FOREIGN PATENT DOCUMENTS 4335 2/1969 Japan .................................. 558/451

OTHER PUBLICATIONS

Massie, C. A., 41, (1947), 3044(b).
Jung, et al., 102, J.A.C.S., (1980), pp. 6304–6311.

Primary Examiner—Joseph Paul Brust

[57] ABSTRACT

A novel process is disclosed for the preparation of 3-pyrrolidinol compounds selected from the group having the formula:

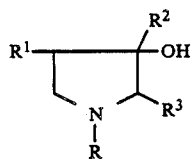

wherein: R is selected from hydrogen, loweralkyl, loweralkenyl, cycloalkyl, cycloalkyl-loweralkyl, phenyl-loweralkyl and substituted phenyl-loweralkyl; $R^1$, $R^2$, and $R^3$ are selected from hydrogen, loweralkyl, and loweralkenyl; and the optical isomers thereof. In the process, 4-amino-3-hydroxybutyronitriles are reductively cyclized with Raney nickel to produce the 3-pyrrolidinol compound.

4 Claims, No Drawings

PROCESS FOR PREPARING 3-PYRROLIDINOLS

This is a division, of U.S. patent application Ser. No. 06/923,544, filed Oct. 26, 1986, now abandoned.

BACKGROUND OF THE INVENTION

1. Field of Invention

The present invention relates to a novel process for preparation of 3-pyrrolidinols, optionally substituted in the 1, 2, 3 and 4 positions and to certain novel 4-amino-3-hydroxybutyronitrile chemical intermediates therefor. The process involves reductive cyclization of 4-amino-3-hydroxybutyronitriles, Raney nickel being the required catalyst.

2. Information Disclosure Statement

Heretofore, several routes to pyrrolidinols have been available for use as described in U.S. Pat. Nos. 2,838,521 and 2,882,276 and in SYNTHETIC COMMUNICATIONS 13 (13) 1117–1123 (1983).

These methods include:

(1) Commercial conversion of 1, 2, 4-butanetriol to 1,4-dibromo-2-butanol with hydrogen bromide at 140° C. followed by condensation with a secondary amine. Debenzylation of N-benzyl-3-pyrrolidinol so produced with hydrogen over palladium on carbon leads to 3-pyrrolidinol;

(2) Reduction of N-substituted-3-pyrrolidinones with lithium aluminum hydride;

(3) Heating cis 1,4-dichloro-2-butenes with benzylamine to produce N-benzyl-3-pyrrolidinol and debenzylating as in (1) above; and (4) Heating malic acid with benzylamine in ethanol at 170° C. to give N-benzyl-3-hydroxysuccinimide and reducing with lithium aluminum hydride to give N-benzyl-3-pyrrolidinol.

Japanese Patent No. 32766 (1985) discloses reductive cyclization of 2-cyanoethylglycine ethyl ester using palladium on carbon catalyst and hydrogen at 50° C. and 10 kg/cm² pressure for 3 hr. In contrast, in the present invention a different class of reactant and product are involved, the end product being a 3-pyrrolidinol and in further contrast, hydrogenation over palladium on carbon catalyst alone did not produce the cyclization brought about by Raney nickel catalyst in the present invention.

One chemical intermediate useful in the process of the present invention; namely, 4-amino-3-hydroxybutyronitrile is a known compound as reported by Jung, M. E. in J. AMER. CHEM. SOC. 102, 6304 (1980). The carbonate of this compound has been used as an intermediate for the manufacture of α-amino-β-hydroxybutyric acid as disclosed in JAP. 16,504(66) (C.A. 66, 18309v). 4-Azido-3-hydroxybutyronitrile also useful in the process is known.

British Patent No. 913,856 (C.A. 59, 1787) describes the preparation of 4-(N-methyl-N-phenylamino)-3-hydroxybutyronitrile from 4-(N-methyl-N-phenyl)-3-hydroxybutyl chloride and sodium cyanide in ethanol. The compound is useful in dye preparation. The foregoing anilino derivative is not useful in the process of the present invention as it cannot be reductively cyclized in the process, nor can the phenol radical be removed as can the benzyl radical.

The use of N,N-diethylamino-3-hydroxybutyronitrile in the preparation of high molecular weight therapeutic agents has been described in IOWA STATE COLL. J. SCI. 21, 41–45 (1946) (C.A. 41, 3044b). The compound is not useful in the process of the present invention as it cannot be cyclized thereby.

Compounds prepared by the process of the present invention are useful in the preparation of pharmaceuticals as described in the following U.S. Pat. Nos.:

U.S. Pat. No. 2,838,521
U.S. Pat. No. 2,830,997
U.S. Pat. No. 2,956,062
U.S. Pat. No. 3,301,869
U.S. Pat. No. 2,882,276 and
U.S. Pat. No. 4,592,866

OBJECTS AND SUMMARY OF THE INVENTION

The present invention is especially concerned with a novel economical process for preparing N-alkyl-3-pyrrolidinols, especially N-methyl- and N-ethyl-3-pyrrolidinols and certain homologs all encompassed by the general formula:

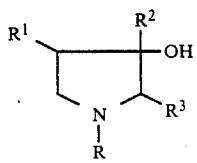

Formula I wherein
R is selected from:
hydrogen,
loweralkyl (1–8 C),
loweralkyl (2–8 C),
cycloalkyl (3–9 C),
cycloalkyl-loweralkyl (4–13 C),
phenyl-loweralkyl (7–14 C), and
(Y)$_{1-3}$-substituted-phenyl-loweralkyl (7–14 C),
R$^1$, R$^2$, and R$^3$ are selected from hydrogen, loweralkyl (1–8 C) or loweralkenyl (2–8 C),
Y is selected from loweralkyl, loweralkoxy, halo or trifluoromethyl, and the optical isomers thereof.

In the first phase of the process the compounds are present as acid addition salts in solution.

The 4-amino-3-hydroxybutyronitrile chemical intermediates used to prepare compounds of Formula I by reductive cyclization with hydrogen and Raney nickel catalyst of Formula I have the formula:

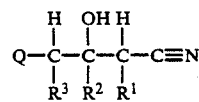

Formula II wherein Q is

or N$_3$ and wherein R, R$^1$, R$^2$ and R$^3$ are as defined under Formula I and the optical isomers and acid addition salts thereof. Compounds other than wherein Q is —N$_3$ (i.e. azido) or NH$_2$— have not previously been reported in the prior art literature. The group of novel compounds encompassed by Formula II have the formula:

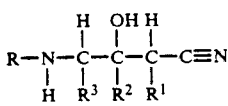

Formula IIa wherein R, R¹, R² and R³ are as defined under Formula I above, except R is not hydrogen, and the optical isomers and acid addition salts thereof.

Novel precursors to the Formula IIa compounds are the amine protected compounds having the formula:

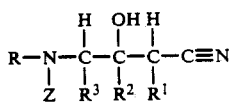

Formula III wherein R, R¹, R² and R³ are as defined under Formula I, and Z is a suitable amine protecting group, preferably selected from:
benzyl,
diphenylmethyl,
α-methylbenzyl,
benzyloxycarbonyl,
diphenylmethoxycarbonyl,
β, β, β-trichloroethoxycarbonyl,
t-butyloxycarbonyl, or
isobutoxycarbonyl,
with the proviso R may be hydrogen only when Z is benzyl, and the optical isomers and acid addition salts thereof.

Formula IV represents a composite of novel compounds of Formula IIa and III combined:

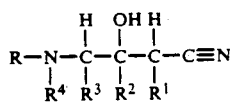

Formula IV wherein R is selected from the group consisting of
loweralkyl (1–8 C),
loweralkenyl (2–8 C),
cycloalkyl (3–9 C),
cycloalkyl-loweralkyl (4–13 C),
phenyl-loweralkyl (7–14 C),
(Y)$_{1-3}$-substituted-phenyl-loweralkyl (7–14 C),
wherein Y is selected from loweralkyl, loweralkoxy, halo or trifluoromethyl; and
R¹, R² and R³ are selected from hydrogen, loweralkyl (1–8 C) or loweralkenyl (2–8 C);
R⁴ is hydrogen or Z wherein Z is a suitable amine protecting group, preferably selected from
benzyl,
diphenylmethyl,
α-methylbenzyl,
benzyloxycarbonyl,
diphenylmethoxycarbonyl,
β, β, β-trichloroethoxycarbonyl,
t-butyloxycarbonyl, or
isobutoxycarbonyl,
and the optical isomers and acid addition salts thereof.

In the further definition of symbols in the formulas hereof and where they appear elsewhere throughout this specification and in the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec. butyl, tert. butyl, amyl, isoamyl, hexyl, heptyl, and octyl radicals and the like. The term "loweralkoxy" refers to -O-loweralkyl.

The term "loweralkenyl" as used herein refers to 2–8 carbon chain hydrocarbon radicals having a carbon-to-carbon double bond, including such as allyl and isobutenyl radicals.

The term "cycloalkyl" as used herein includes primarily cyclic alkyl radicals containing 3–9 carbon atoms inclusive and includes such groups as cyclopropyl, cyclobutyl, cyclopentyl, cyclohexyl, methylcyclohexyl, cycloheptyl and the like.

The terms "halo", "halide" or "halogen" when referred to herein include fluorine, chlorine, bromine, and iodine unless otherwise stated.

The term "non-interfering radicals" when used in conjunction with phenyl substitution is intended to mean a radical which does not interfere with any of the reactions including reductive cyclization process involving Raney nickel.

The term "reactive leaving group" refers to any of the conventional radicals such as halo, -o-tosyl or o-mesyl which may be used to introduce a cyano group by reacting with metal cyanide reagents.

The term "amine protecting group" refers to a radical which temporarily prevents unwanted reaction with the hydrogen of an amine function, such protecting group being removable in a subsequent step referred to as "deprotection." Representative of such amine protecting groups which suitably protect and can be suitably removed without disrupting the integrity of the 4-amino-3-hydroxybutyronitrile chemical intermediates involved are those of two general classes (a) and (b) as follows:

(a) Urethane Derivatives. Examples of suitable urethane forming radicals which can be used for protection and the method of "deprotection" are as follows:
t-butoxycarbonyl (deprotect with acid),
isobutyloxycarbonyl (deprotect with ammonia and pyridine),
β, β, β-trichloroethoxycarbonyl (deprotect with zinc and acetic acid), or
benzyloxycarbonyl (deprotect with strong acid, e.g., HCl, HBr, HI or hydrogenation);

(b) Benzyl Derivatives. Examples of suitable benzyl forming radicals which can be used for protection and the method of "deprotection" are as follows:
phenylmethyl (deprotect by hydrogenation over Pd/C),
α-methylbenzyl (deprotect by hydrogenation over Pd/C), or
diphenylmethyl (deprotect by hydrogenation over Pd/C).

Reference is made to the textbook: "Protective Groups in Organic Chemistry by J. F. W. McOmie, publ. Plenum Press London & New York (1973), pp. 43–74", for discussion of protection and deprotection of primary and secondary amines.

In such amine protecting groups having a phenyl compound, the phenyl may be substituted by non-interfering radicals such as do not poison the Raney nickel catalyst or waste hydrogen gas by uptake thereof. Deprotection is accomplished by a suitable agent as explained hereinbelow.

The term "non-interfering acid" as used herein refers to an acid which does not poison the catalyst within the working range of pH 3-10.

The term "acid containing solution" specifies an acid has been added to the solution irrespective of the manner of addition, e.g., as solution, as a gas, or as acid addition salt of reactant, etc.

The term "reductive cyclization" and "reductively cyclizing" are terms referring to the act of reducing the nitrile group of a 4-amino-3-hydroxybutyronitrile and causing cyclization to the 3-pyrrolidinol.

It is therefore an object of the present invention to provide a novel improved process for the preparation of 3-methylpyrrolidinol and analogs thereof.

Another object is to provide novel chemical intermediates, certain N-substituted-4-amino-3-hydroxybutyronitriles, and methods of production thereof.

Additional objects will be apparent to one skilled in the art and still others will become apparent hereinafter.

DETAILED DESCRIPTION OF THE INVENTION

The novel process for preparing the 3-pyrrolidinols of Formula I from 4-azido or 4-amino-3-hydroxybutyronitriles is schematically represented by Chart I.

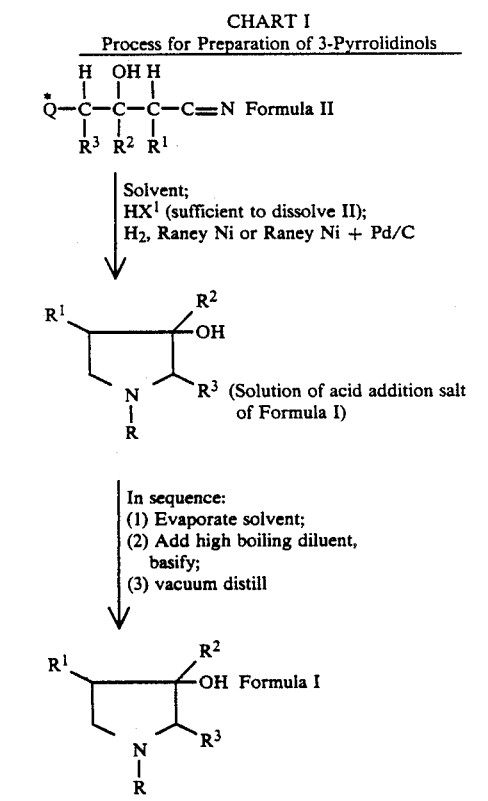

Footnote to Chart I:
*Q is R—N— or N₃ (azido), and R, R¹, R² and R³
         |
         H
are as defined under Formula I: HX¹ is a noninterfering acid. Optical (R) and (S) isomers potentially available due to chiral center at the carbon bearing the hydrogenation group.

Briefly stated, the novel process for preparing the free base of the 3-pyrrolidinols of Formula I is comprised of the steps of:

Step 1, subjecting a hydroxybutyronitrile compound selected from the group having the formula:

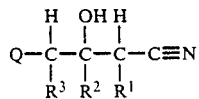

wherein $R^1$, $R^2$, and $R^3$ are as defined hereinabove under Formula I; Q is

or N₃ (i.e, azido) and wherein R is as defined under Formula I and the optical isomers thereof in an acid containing solution having dissolved therein a non-interfering acid: HX¹, the acid optionally alternatively supplied by substituting an acid addition salt of compound II, to hydrogen gas under pressure in the presence of a catalyst comprised of Randy nickel or optionally a mixture of Raney nickel and palladium on carbon to give a slurry comprised of:
(a) a solution having dissolved therein a pyrrolidinol compound having the formula

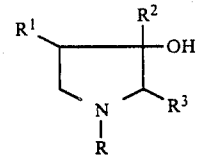

wherein R, $R^1$, $R^2$, and $R^3$ are as defined above, and
(b) the catalyst in suspension and separating the catalyst from the slurry to give said pyrrolidinol compound in acid containing solution, and Step 2, isolating the free base of the 3pyrrolidinols of Formula I by the sequential procedure of
(a) evaporating off the reaction solvent,
(b) adding high boiling diluent and base, to neutralize the acid, giving the free base of the 3-pyrrolidinol, and,
(c) vacuum distilling the free base of said pyrrolidinol compound.

The invention encompasses the process for the preparation of the acid containing solution of the pyrrolidinol compounds of Formula I of Step 1 by itself and the combination of Steps 1 and 2 together to give the free base pyrrolidinol compounds of Formula I.

The following general description is applicable to the foregoing process.

In the process, a compound of Formula II in a suitable solvent having an acidic component (Formula II compound as acid addition salt or added acid HX¹ if free base is used in amount sufficient to dissolve II), the solvent described as being capable of dissolving some water and preferably having water dissolved therein and the resulting solution having a pH of about 3-10, preferably about 5-7, is subjected to hydrogen gas under pressure at about 15-150 psi, preferably about 25-75 psi and about 0-100° C. temperature, preferably 20-50° C. in the presence of Raney nickel catalyst, optionally and preferably in the presence of Raney nickel and palladium on carbon catalysts until hydrogen uptake ceases and the compound of Formula II is substantially reductively cyclized to give a compound of Formula I as an acid salt in solution. The Formula I compound is then isolated by substantially removing the reaction solvent, adding a diluent carrier, neutralizing (or basifying) the acid salt and any excess HX¹ acid and vacuum distilling the Formula I free base.

The following more detailed description is also applicable to the process of the invention.

In Step 1, suitable solvents are those which will dissolve both the starting compound of Formula II and the product compound of Formula I, both in the presence of an acid, such acid being non-poisonous to the catalyst and in amount such that solubilization of compound II is attained and maintained, and the Raney nickel is not inactivated due to amount of acid. Suitable representative acids are mineral acids such as hydrochloric, hydrobromic, sulfuric or organic acids such as acetic acid or trifluoroacetic acid. Ratios of about 0.9 to 1.1 equivalents of acid per mole of compound II appear optimum and are therefore preferred. Above about 1.1 equivalent ratio of acid to compound II, Raney nickel is inactivated. As stated above, suitable solvents appear to have capacity to dissolve, at least, some water, although water may not be required in some solvents such as methanol or ethanol. However, it appears desirable to have at least a small amount of water present and as much as 100% water may be used. The use of too much water increases difficulty in isolation of the product. Ratios of the lower alkanols to water in the ratio range of 70:30 to 90:10 volume % are preferred. Solvent mixtures comprised of isopropanol and water in the ratio range of 70:30 to 90:10 volume % are especially preferred. Suitable operating concentrations of starting compound II to liquid appear to be in the range of 5-25-weight %, preferably about 10 weight %.

Raney nickel is the required catalyst, palladium on carbon by itself being ineffective alone in the reductive cyclization. When the starting Formula II compound is derived by deprotecting the amino group of compound III by hydrogenation over palladium on carbon catalyst, it has been found preferable to conduct Step 1 of the process without separating the palladium on carbon catalyst as a higher yield was obtained when the palladium catalyst was left in. The preferred catalyst is a mixture of Raney nickel and palladium on carbon.

Compounds of Formulas I, II, and III have a chiral center at the carbon bearing the hydroxy radical. Preparation of an enantiomer is accomplished by starting with an appropriate optically active epoxide such as that of epichlorhydrin or glycidyl tosylate and the like and preparing the (R) and (S)-4-(N-R)- wherein N-R is an amino radical and (R) and (S) are the enantiomer designations -3-hydroxybutyronitrile which is reductively cyclized to give the (R) and (S)-3-pyrrolidinol.

A preferred aspect of the present invention is the reductive cyclization with hydrogen over catalyst comprised of Raney nickel of compounds of Formula II wherein Q is

and R is methyl or ethyl and the compound produced is a pyrrolidinol of Formula Ia or Formula Ib having the structures:

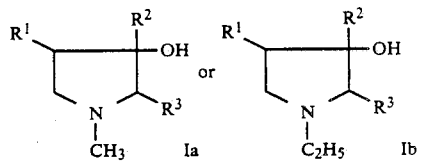

Two most preferred aspects of the invention is the reductive cyclization with hydrogen in the presence of catalyst comprised of Raney nickel of the compounds 4-(N-methyl)-3-hydroxybutyronitrile and 4-(N-ethyl)-3-hydroxybutyronitrile to give N-methyl-3-pyrrolidinol and N-ethyl-3-pyrrolidinol.

Starting compounds of Formula II wherein Q is $N_3$ are prepared by the known method represented by the following equations shown illustratively for compounds wherein $R^1$, $R^2$, and $R^3$ are all hydrogen, but the method is not limited to hydrogen radicals:

$$ClCH_2CHOHCH_2Cl + NaCN \rightarrow ClCH_2CHOHCH_2CN,$$

G. Braun, J. Amer. Chem. Soc. 52, 3167

$$ClCH_2CHOHCH_2CN + NaN_3 \rightarrow N_3CH_2CHOHCH_2CN \qquad \text{IIc}$$

Starting compound of Formula II wherein Q is $NH_2$ are available by the known method represented by the following equation also shown illustratively for $R^1$, $R^2$, and $R^3$=hydrogen, but the method is not limited to hydrogen radicals:

$$N_3CH_2CHOHCH_2CN \xrightarrow{\text{reduce}} H_2NCH_2CHOHCH_2CN \qquad \text{IIb}$$

Intermediate chemical compounds of Formula IIa may be prepared by the reaction sequence outlined in Chart II.

CHART II

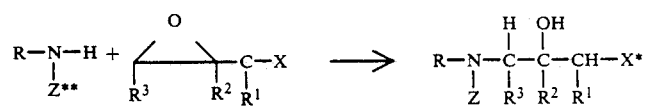

(R is other than H)

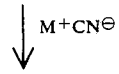

CHART II

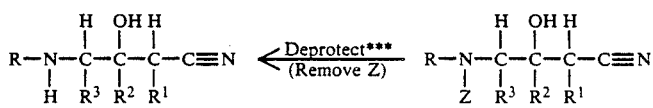

IIa                          III

Footnotes to Chart II:

*X is any reactive leaving group such as halo, —O-tosyl or —O-mesyl.

**Z is an amine protecting group, e.g., benzyl, diphenylmethyl, α-methylbenzyl, benzyloxycarbonyl, diphenylmethoxycarbonyl, β,β,β-trichloroethoxycarbonyl t-butoxycarbonyl and isobutoxycarbonyl;

***benzyl, diphenylmethyl and α-methylbenzyl radicals are removed by hydrogenation over palladium on carbon in the presence of acidic protic solvent; benzyloxycarbonyl and t-butoxycarbonyl radicals are removed with acid; and the trichloroacetoxycarbonyl radical is removed with zinc and acetic acid. Compounds wherein R is benzyl may be obtained, for example, from a compound of Formula III wherein R is benzyl and Z is β,β,β-trichloroethoxycarbonyl and the deprotecting agent is zinc + acetic acid which leaves benzyl intact.

Selected alternative methods for preparing compounds of Formula II are illustrated schematically in Chart III.

CHART III

Alternate Method A:

H$_2$NCH$_2$CHOHCH$_2$CN + R*CHO     $\xrightarrow[\text{e.g., catalyst + H}_2 \text{ or NaBH}_4]{\text{reductive alkylation}}$ or R*R$^4$C(O)

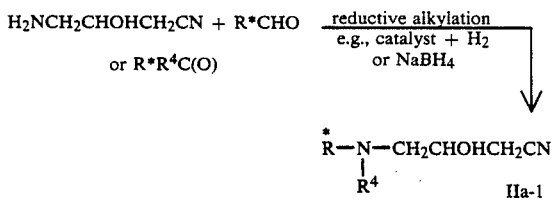

IIa-1

Alternate Method B:

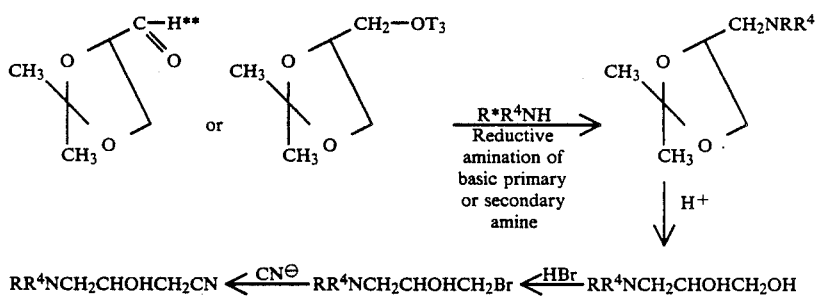

Alternate Method C:

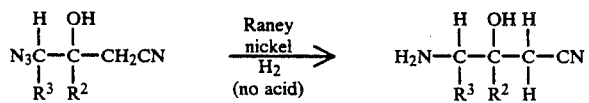

Alternate Method D:

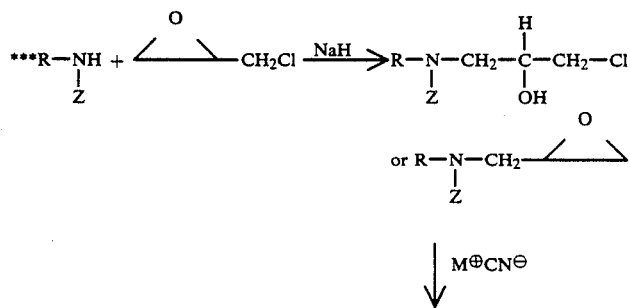

-continued
CHART III

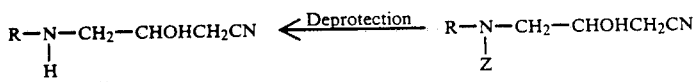

Footnotes to Chart III:
*R is as defined under Formula I.
**These starting compounds may be prepared by the method of Jung, M. E. et al., J. Amer. Chem. Soc. 102, 6304(1980).
***R is as defined under Formula I.
Z is selected from —C(O)OCH$_2\phi$
—C(O)OCH$_2$CCl$_3$
—C(O)O-t-Butyl Epixode starting reactants of Chart II are available commercially or can be made by methods known in the art. A particularly versatile method is epoxidation of an appropriate allylic alcohol employing titanium tetraisopropoxide. See [The Merck Index 10th Ed (1983), page ONR-83] followed by displacement of the hydrogen of the hydroxyl group with a tosyl group. If desired, the resulting O-tosyl group may be replaced by a halo radical by reacting with an alkali-metal halo salt.

Starting epoxides wherein R$^1$ or R$^2$ or R$^3$ are methyl are known compounds and base catalyzed isomerism of these compounds has been studied, J. HETEROCYCLIC CHEMISTRY 6 (1969) pp 651–654. The compounds are:
Epichlorohydrin,
1-chloro-2,3-epoxy-2-methylpropane,
1-chloro-2,3-epoxybutane, and
3-chloro-1,2-epoxybutane The method of preparation of (DL)-4-azido-3-hydroxybutyronitrile and (R)-4-azido-3-hydroxybutyronitrile shown by Jung, M. E. and Shaw, T. J., in J. AM. CHEM. SOC. (1980) 102, pp 6304–6311 illustrates preparation of starting azido compounds. In that reference dl-4-tosyloxy-3-hydroxybutanenitrile or (R)-4-mesyloxy-3-hydroxybutanenitrile are reacted with potassium azide in acetonitrile.

The following intermediates, examples, and the preceding description and charts serve to illustrate the preparation of chemical intermediates and the process of the invention; however, the scope of the invention is not limited thereto.

INTERMEDIATE 1

4-(N-Methyl-N-benzylamino)-3-hydroxybutyronitrile

To a stirred, cooled solution of 79 ml (1.0 mole) of epichlorohydrin in 600 ml of 200 proof ethanol was added 133 ml (1.0 mole) of N-(methyl)benzylamine, keeping the reaction mixture at 3° to 5° C. Addition time was 18min. The temperature of the reaction mixture was allowed to rise to 29° C. over a 2 hr period and then raised to 37° C. briefly. Proton NMR analysis indicated about 10% of the N-methylbenzylamine was unreacted. An additional 7.9ml (0.1 mole) of epichlorohydrin was added and the temperature was raised to 37° C. briefly. One hour later, 65 g (1.3 mole) of sodium cyanide in 150 ml of water was added over a 2 min period at 32° C. The reaction mixture was stirred overnight without heating or cooling. The mixture was heated to reflux for one hour and concentrated. The concentrate was diluted with methylene chloride and water. The organic layer was separated and washed once with sodium chloride solution. The aqueous layers were back extracted with a fresh portion of methylene chloride. The organic layers were combined, dried, filtered and evaporated to give 224.9 g of dark brown oil. Proton NMR showed mainly the title compound was present with some solvent. (DCCl$_3$, ppm): 7.35 (singlet, phenyl protons), 4.15 to 3.35 (multiplet, methine proton on carbon 3, hydroxyl proton on oxygen and the benzylic protons), 2.65 to 2.20 (multiplet, methylene protons on carbons 2 and 4 and the methyl protons on the amino group).

INTERMEDIATE 2

4-(N-Ethyl-N-benzylamino)-3-hydroxybutyronitrile

In a procedure similar to Example 1, the title compound was prepared in 94% yield from 1 mole of N-ethylbenzylamine. Proton NMR analysis showed mainly product present with some solvent. (DCCl$_3$, ppm): 7.35 singlet, phenyl protons), 4.10 to 3.40 (multiplet, methine proton on carbon 3, hydroxyl proton on oxygen, and the benzylic portons) 2.80 to 2.30 (multiplet methylene protons on carbons 2 and 4 and methylene protons on the ethyl group), 1.10 (triplet, methyl protons on the ethyl group).

INTERMEDIATE 3

4-Methylamino-3-hydroxybutyronitrile hydrochloride [1:1]

4-(N-Methyl-N-benzylamino)-3-hydroxybutyronitrile, 5.1 g (0.02 mole) was dissolved in 40 ml of isopropanol and 0.5 g of 5% palladium on carbon was added to the solution. The mixture was subjected to hydrogen gas under about 55 psi for 18 hr at 60° C. Mass spectrometry of a sample taken from the mixture indicated no reduction had occurred. About 2.1 ml (ca. 0.02 mole) of 37% hydrochloric acid and 0.5 g of 5% palladium on carbon were added and the mixture was subjected to hydrogen gas under 50 psi for 18 hr at room temperature. Approximately 0.02 molar equivalents of hydrogen was absorbed. A sample taken for mass spectroscopy showed product (m/e 115) and a small amount of starting material (m/e 205) unreacted. The mixture was filtered and the filtrate was concentrated to a light yellow liquid weighing 4.73 g. Proton NMR analysis showed mainly 4-methylamino-3-hydroxybutyronitrile and a small amount of starting benzyl compound and solvent was present, NMR analysis is as follows: (D$_2$O, ppm): 4.40 (multiplet, methine proton on carbon 3), 3.20 (multiplet, methylene protons on carbon 4 bearing the protonated amino groups), 2.80 (multiplet, methylene protons on carbon 2 and methyl protons on the amino group).

INTERMEDIATE 4

4-Azido-3-hydroxybutyronitrile

A mixture of 48 g (0.40 mole) of 4-chloro-3-hydroxybutyronitrile, 52 g (0.080 mole) of sodium azide, 4.8 g of tetra-n-butylammonium bromide, 250 ml of chloroform and 100 ml of water was stirred while heating under reflux for 32 hr. The organic layer was separated and set aside. The aqueous layer was saturated with 4.8 g of potassium carbonate and then extracted three times with methylene chloride. The methylene chloride extracts were combined with the above organic layer and the solution was dried over anhydrous sodium sulfate and the mixture was filtered. The filtrate was evaporated to give a brown oil weighing 49.46 g, a 98% yield based on the crude. Proton NMR showed signals for the desired product and a small amount of tetra-n-butylammonium salt: (CDCl$_3$, ppm): 7.20 (singlet, chloroform), 4.35 to 3.90 (pentet, methine proton of product), 3.85 (singlet, hydroxyl proton of product), 3.45 (doublet, methylene protons next to the azide group of the product), 2.60 (doublet, methylene protons next to the cyano group of the product), 3.25 to 2.85 and 1.90 to 0.80 (multiplets, signals from about 4% of tetra-n-butylammonium salt).

INTERMEDIATE 5

4-Amino-3-hydroxy-butyronitrile

To 22.5 g (0.178 mole) of 4-azido-3-hydroxy-butyronitrile (prepared in Intermediate 4) dissolved in 130 ml of isopropanol and 13 ml of water was added 2.5 g of Raney nickel catalyst. The mixture was hydrogenated at room temperature on a Parr ® hydrogenator. A sample drawn at 2 hr reaction time showed by Mass spectrum analysis both starting material (m/e 127) and 4-amino-3-hydroxy-butyronitrile (m/e 101). Another sample taken at 4 hr reaction time showed by Mass spectrum analysis mainly(m/e 101) and a trace of(m/e 127).

EXAMPLE 1

N-Ethyl-3-pyrrolidinol 4-(via 4-(N-ethylamino)-3-hydroxybutyronitrile)

4-(N-Ethyl-N-benzylamino)-3-hydroxybutyronitrile, 109 g (0.50 mole), was dissolved in isopropanol and water. The solution was cooled and mixed with 41.6 ml (0.50 mole) of 37% hydrochloric acid. Catalyst (11 g, 5% palladium on carbon) was wetted with water and rinsed into the mixture with isopropanol. Total volumes of isopropanol and water were 800 ml and 80 ml respectively. The mixture was subjected to hydrogen under about 50 psi until absorption of hydrogen ceased, (0.50 mole). Mass spectroscopy of a sample indicated all starting compound had debenzylated, giving 4-(N-ethylamino-3-hydroxybutyronitrile in the mixture. Raney nickel, 11 g (rinsed with water twice), was added to the mixture. This mixture was subjected to 50 psi hydrogen pressure at room temperature until absorption of hydrogen ceased. The mixture was filtered and the filtrate was concentrated to give light brown oil. To the oil was added 75 ml of polyethylene glycol 400, 32 g (0.4 mole) of 50% sodium hydroxide solution, 27.6 g (0.2 mole) of potassium carbonate and some methanol used in rinsing. The mixture was stirred, concentrated and then vacuum distilled to give 31.0 g (54%) of main fraction, distilling at 1 to 5 Hg and 65 to 75° C., the title compound. Analysis by proton NMR (D$_2$O, ppm) obtained was as follows: 4.80 (singlet, HOD), 4.40 (multiplet, methine proton), 3.10 to 1.30 (multiplets, all the methylene protons), 1.10 (triplet, methyl protons of the ethyl group).

EXAMPLE 2

N-Methyl-3-pyrrolidinol (via 4-(N-methylamino)-3-hydroxy-butyronitrile)

4-(N-Methyl-N-benzylamino)-3-hydroxybutyronitrile was debenzylated to 4-(N-methylamino)-3-hydroxy-butyronitrile which was converted to the title compound in 56% overall yield by the procedure of Example 1. The product distilled at 1-5 mm Hg and 40 to 50° C. Analysis by proton NMR (D$_2$O, ppm) obtained was as follows: 4.80 (singlet, HOD), 4.40 (multiplet, methine proton), 3.00 to 1.30 (multiplets and a singlet, the singlet is the methyl protons of the N-methyl group. The multiplets are the methylene protons. The foregoing spectrum matches with the spectrum of an authentic sample of N-methyl-3-pyrrolidinol.

EXAMPLE 3

3-Pyrrolidinol (via 4-amino-3-hydroxybutyronitrile)

A solution of 22.5 g (0.178 mole) of 4-azido-3-hydroxy-butyronitrile in 130 ml of isopropanol and 13 ml of water together with 2.5 g Raney nickel was subjected to hydrogen at room temperature in a Parr hydrogenator for 4 hr. Mass spectrum analysis indicated only a trace of starting material m/e 127 was unreacted, the main product exhibiting m/e 101, that of 4-amino-3-hydroxybutyronitrile.

The mixture was made slightly acidic by adding 13.6 ml of 37% hydrochloric acid, and 1.0 g of additional Raney nickel was added. The mixture was subjected to 50 psi hydrogen pressure overnight, without hydrogen uptake occurring. The mixture was filtered and 2.5 g of fresh Raney nickel was added to the filtrate. The mixture was hydrogenated at room temperature and about 50 psi; hydrogen uptake occurred and sampling for mass spectrum analysis indicated the material present was mainly 3-pyrrolidinol (m/e 88). The catalyst was removed by filtration and the filtrate was evaporated to give a brown oil. To the oil were added 30 ml of polyethyleneglycol-400, 8 g (0.1 mole) of 50% aqueous sodium hydroxide solution, 11 g (0.08 mole) of potassium carbonate and some methanol for rinsing. The resultant mixture was stirred for a period of time to assure acid neutralization and then concentrated on a rotary evaporator. The concentrate was vacuum distilled. The desired product, 3-pyrrolidinol, was collected from the still at 80-120° C. under 5 to 20 mm Hg pressure. Weight of product liquid obtained was 4.7 g (30% yield). Proton NMR (D$_2$O, ppm) analysis obtained was as follows: 4.85 (singlet, HOD the hydroxyl and the amino proton), 4.55 to 4.25 (multiplet, methine proton) 3,85 to 2.50 (multiplet, methylene protons on carbons 2 and 5, both are next to the nitrogen.) 2.30 to 1.40 (multiplet, methylene protons at carbon 4).

EXAMPLE 4

(R)-N-Methyl-3-pyrrolidinol and (S)-N-Methyl-3pyrrolidinol

2-R-(+)-Glycidyl tosylate and 2-S-(−)-glycidyl tosylate available from the Aldrich Chemical Co., P. O. Box 355 Milwaukee, Wis. 53201, USA, in 200 proof ethanol are separately reacted with N-(methyl)benzyl amine as in Intermediate 1, and the products thereof are each reacted with sodium cyanide as in Intermediate 1 and isolated as the optically active (R) and (S)-4-(N- methyl-N-benzylamino)-3-hydroxybutyronitriles. These nitriles are hydrogenated over palladium on carbon in acidic isopropanol and water solution and the resulting secondary 4-methylamino-3-hydroxybutyronitriles reductively cyclized by hydrogenation over Raney nickel as in Example 1 to give the title compounds.

EXAMPLE 5

(R)-N-Methyl-3-pyrrolidinol (S)-Epichlorohydrin is reacted with N-(methyl)benzyl amine and the product thereof is reacted with sodium cyanide as in Intermediate 1 and isolated as the optically active R-4-(N-methyl-N-benzylamino)-3-hydroxybutyronitrile. This nitrile is hydrogenated over palladium on carbon in acidic isopropanol and water solution and the resulting 4-methylamino-3-hydroxybutyronitrile is reductively cyclized by hydrogenation over Raney nickel to give the title compound.

N,4-Dimethyl-3-pyrrolidinol and N,2-Dimethyl-3-pyrrolidinol

Following the procedure of Intermediate 1, 2, 3-epoxybutyl chloride is reacted with N-(methyl)benzylamine. Sodium cyanide is added. The products of these reactions are expected to be
4-[N-(methyl)benzylamino]-4-methyl-3-hydroxybutyronitrile, and
4-[N-(methyl)benzylamino]-2-methyl-3-hydroxy butyronitrile.
When these nitriles are deprotected to remove the benzyl radical by hydrogenation over palladium on carbon and the products thereof are reductively cyclized with hydrogen over Raney nickel, the title compounds are obtained. When the products are present in a mixture, they are separated by Spinning Band Column Distillation.

EXAMPLE 7

N,3-Dimethyl-3-pyrrolidinol.

Following the procedure of Example 2 and substituting 4-(N-methylamino)-3-hydroxy-3-methyl-butyronitrile for 4-(N-methylamino)-3-hydroxybutyronitrile, the title compound is obtained.

EXAMPLE 8

N,4-Dimethyl-3-pyrrolidinol.

Following the procedure of Example 2 and substituting 4-(N-methylamino)-3-hydroxy-2-methyl-butyronitrile for 4-(N-methylamino)-3-hydroxybutyronitrile, the title compound is obtained.

What is claimed is:

1. A compound selected from the group having the formula:

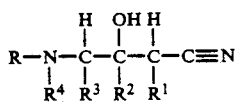

wherein
R is selected from the group consisting of
loweralkyl (1–8 C),
loweralkenyl (2–8 C),
cycloalkyl (3–9 C),
cycloalkyl-loweralkyl (4–13 C),
phenyl-loweralkyl (7--C), or
(Y)$_{1-3}$-substituted-phenyl-loweralkyl (7–14 C);
R$^1$, R$^2$ and R$^3$ are selected from hydrogen, loweralkyl (1–8 C), or loweralkenyl (2–8 C);
R$^4$ is hydrogen or an amine protecting radical selected from
benzyl,
diphenylmethyl,
α-methylbenzyl,
benzyloxycarbonyl,
diphenylmethoxycarbonyl,
β, β, β,-trichloroethoxycarbonyl,
isobutoxycarbonyl or t-butyloxycarbonyl;
Y is selected from loweralkyl, loweralkoxy, halo or trifluoromethyl;
either R or R$^4$ must include an aromatic ring;
and the optical isomers and acid addition salts thereof.

2. The compound of claim 1 which is 4-(N-methyl-N-benzylamino)-3-hydroxybutyronitrile or an acid addition salt thereof.

3. The compound of claim 1 which is 4-(N-ethyl-N-benzylamino)-3-hydroxybutyronitrile or an acid addition salt thereof.

4. A compound selected from the group having the formula:

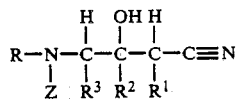

wherein R is selected from
hydrogen
loweralkyl (1–8 C),
loweralkyl (2–8 C),
cycloalkyl (3–9 C),
cycloalkyl-loweralkyl (4–13 C),
phenyl-loweralkyl (7–14 C), or
(Y)$_{1-3}$-substituted-phenyl-loweralkyl (7–14 C);
wherein Y is selected from loweralkyl, loweralkoxy, halo or trifluoromethyl,
R$^1$, R$^2$ and R$^3$ are selected from hydrogen, loweralkyl (1–8 C), or loweralkenyl (2–8 C);
Z is an amine protecting group selected from
benzyl,
diphenylmethyl,
α-methylbenzyl,
benzyloxycarbonyl,
diphenylmethoxycarbonyl,
β, β, β,-trichloroethoxycarbonyl,
t-butyloxycarbonyl,
isobutoxycarbonyl;
with the proviso R may be hydrogen only when Z is benzyl and either R or Z must include an aromatic ring;
and the optical isomers and acid addition salts thereof.

* * * * *